(12) United States Patent
Delval

(10) Patent No.: US 9,931,178 B2
(45) Date of Patent: Apr. 3, 2018

(54) CUTTING INSTRUMENT, IN PARTICULAR DENTAL INSTRUMENT

(71) Applicant: MAILLEFER INSTRUMENTS HOLDING Sàrl, Ballaigues (CH)

(72) Inventor: Alain Delval, Le Brassus (CH)

(73) Assignee: DENTSPLY SIRONA Inc., York, PA (US)

( * ) Notice: Subject to any disclaimer, the term of this patent is extended or adjusted under 35 U.S.C. 154(b) by 167 days.

(21) Appl. No.: 15/095,726

(22) Filed: Apr. 11, 2016

(65) Prior Publication Data

US 2016/0302882 A1 Oct. 20, 2016

(30) Foreign Application Priority Data

Apr. 16, 2015 (EP) ..................................... 15163782

(51) Int. Cl.
| | | |
|---|---|---|
| *A61B 17/00* | (2006.01) | |
| *A61C 3/02* | (2006.01) | |
| *B23C 5/10* | (2006.01) | |
| *A61B 17/16* | (2006.01) | |

(52) U.S. Cl.
CPC ............ *A61C 3/02* (2013.01); *A61B 17/1615* (2013.01); *A61B 17/1622* (2013.01); *B23C 5/10* (2013.01); *B23C 2210/03* (2013.01); *B23C 2222/28* (2013.01); *B23C 2222/64* (2013.01); *B23C 2222/84* (2013.01); *B23C 2222/88* (2013.01); *B23C 2240/08* (2013.01); *B23C 2240/16* (2013.01)

(58) Field of Classification Search
CPC combination set(s) only.
See application file for complete search history.

(56) References Cited

U.S. PATENT DOCUMENTS

| | | | |
|---|---|---|---|
| 5,882,198 A | 3/1999 | Taylor et al. | |
| 2010/0254779 A1* | 10/2010 | Wedner | ................ B23B 51/009 408/224 |
| 2011/0195377 A1 | 8/2011 | Sun et al. | |

OTHER PUBLICATIONS

International Preliminary Report on Patentability dated Oct. 17, 2017.
International Search Report and Written Opinion of the International Searching Authority dated Jun. 29, 2016.
EP Search Report of corresponding EP Patent 3081186 dated Oct. 19, 2016.

\* cited by examiner

*Primary Examiner* — Sameh Boles
(74) *Attorney, Agent, or Firm* — David A. Zdurne; Douglas J. Hura; Leana Levin

(57) ABSTRACT

The present invention relates to a rotary cutting instrument, in particular of the bur type, intended for chirurgical or dental use and comprising an active cutting part and a handle. Said active part is made of a metal carbide and the handle is made of a nickel-titanium alloy. The instrument further comprises an intermediate part made of stainless steel placed between the active part and the handle and metallurgically connected to said active part and to said handle.

10 Claims, 1 Drawing Sheet

CUTTING INSTRUMENT, IN PARTICULAR DENTAL INSTRUMENT

THE CROSS-REFERENCE TO RELATED APPLICATIONS

Figure 1:
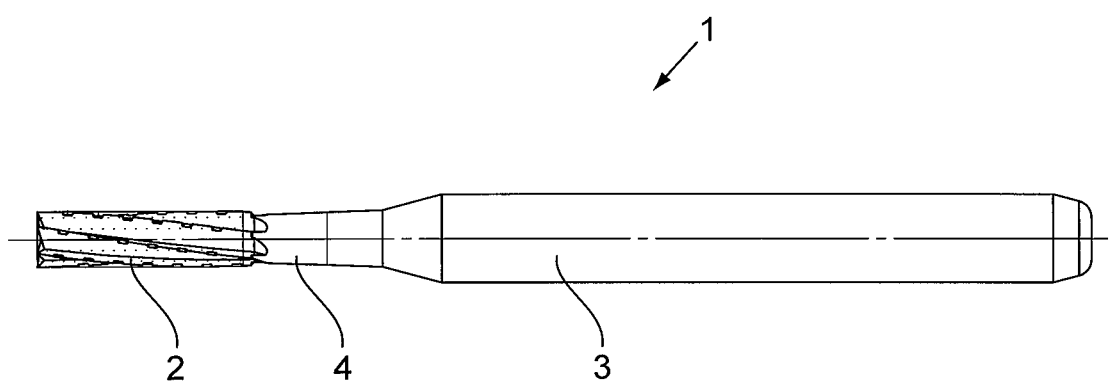

The This patent application claims the benefit of and priority to EP Patent Application Ser. No. 15163782.4, filed on Apr. 16, 2015, which is herein incorporated by reference for all purposes.

TECHNICAL FIELD

The present invention relates to the field of cutting instruments and in particular instruments intended for the medical field such as dental or surgical instruments. More particularly, the invention is targeted towards a rotary cutting instrument such as a bur.

BACKGROUND

A bur can be used, for example, in the medical field for bone surgery or in the dental field for implantology or in endodontic treatments for drilling root canals, shaping stumps, preparing and trimming crowns, preparing cavities, removing dentine, enamel or restorative materials from the tooth such as amalgams, composites, ceramics or metals.

In the field of dentistry and bone surgery, it is known to use burs, at least the active cutting part of which is made of a metal carbide, in particular tungsten carbide. This material is used in particular because of its cutting performance and its durability. In fact, in contrast to carbon steel, the carbide does not corrode and is sufficiently hard for it to be used at high speeds, even for cutting bone. Cutting instruments in which the active part is made of carbide include instruments in which the handle is made of stainless steel or instruments in which the whole instrument formed by the active part and the handle is made from a single piece made of a carbide.

The aim of the present invention is to provide a cutting instrument, in particular a cutting instrument for dental or surgical use of the bur type, the active part of which is made of carbide, in particular tungsten carbide, and the cutting performance of which is increased.

SUMMARY OF THE INVENTION

The object of the present invention is a rotary cutting instrument, in particular of the bur type, comprising an active cutting part and a handle, said active part being made of a metal carbide, characterised in that the handle is made of a nickel-titanium alloy; and in that the instrument further comprises an intermediate part made of stainless steel placed between the active part and the handle and metallurgically connected to said active part and to said handle.

DETAILED DESCRIPTION OF THE DRAWINGS

FIG. 1 illustrates an embodiment of the invention having the form of a bur for dental use.

DETAILED DESCRIPTION OF THE INVENTION

In accordance with a preferred embodiment of the invention, the cutting instrument is a dental instrument and in particular a bur 1 used in implantology or during endodontic treatments for drilling root canals, shaping stumps, preparing and trimming crowns, preparing cavities, removing dentine, enamel or restorative materials from the tooth such as amalgams, composites, ceramics or metals. As an alternative, the cutting instrument in accordance with the invention can also be a surgical instrument intended, for example, for bone surgery.

The bur 1 comprises an active part 2 and a handle 3 intended to be inserted in a motor, in a hand piece or a contra-angle in order for it to be rotationally driven. The shape of the active part 2, its cutting edges, its length, its geometry, etc. will not be described in more detail herein.

In accordance with the invention, the active part 2 is made of a metal carbide and preferably tungsten carbide (WC) whilst the handle 3 is made of a nickel-titanium alloy (NiTi). Nickel-titanium alloys are frequently used in the medical and dental fields, in particular owing to their flexibility. Therefore, the alloy composition forming the handle 3 will not be described in more detail herein.

In accordance with the invention, an intermediate part 4 is inserted between the active part 2 and the handle 3 of the cutting instrument 1. This intermediate part 4 is made of stainless steel and is suitably metallurgically connected to the handle 3 made of nickel-titanium and to the active part 2 made of a carbide. Preferably, the intermediate part 4 is brazed to the active part 2 made of a carbide whilst it is welded to the handle 3 made of nickel-titanium. Generally, the intermediate part 4, the active part 2 and the handle 3 are metallurgically connected to each other by any suitable means known to the person skilled in the art.

The aim of the intermediate part 4 is to allow the connection between the active part 2 made of tungsten carbide and the handle 3 made of nickel-titanium. In fact, it is very difficult to form a metallurgical connection directly between the tungsten carbide and the nickel-titanium.

Preferably, the intermediate part 4 made of stainless steel has a length or thickness between 0.05 and 50 mm, more preferably 1.5 mm. The person skilled in the art is able to determine the suitable length/thickness of the intermediate part 4 allowing an effective connection between the active part 2 made of a carbide and the handle 3 made of nickel-titanium.

The instrument in accordance with the present invention has improved cutting performance, in particular compared with instruments in which the handle is made of steel or a carbide: in fact, the handle 3 made of nickel-titanium is more flexible than a handle made of steel or a carbide. This flexibility allows in particular the production of cutting instruments intended for surgery, in which the handle is sufficiently flexible to allow work in a curved canal. In addition, the flexibility of the handle generates vibrations along the instrument upon use thereof (rotation), said vibrations increasing the cutting performance of the instrument.

A cutting instrument, intended in particular for use in the dental or surgical field, which performs well and combines the advantages of an active part made of a carbide and a handle made of nickel-titanium, is thus obtained.

The invention claimed is:

1. A rotary cutting instrument comprising:
    an active cutting part, the active part being made of a metal carbide;
    an intermediate part, the intermediate part is made of stainless steel; and
    a handle, the handle is made of a nickel-titanium alloy; and
    wherein the intermediate part is located between the active part and the handle and is metallurgically connected to said active part and to said handle.

2. The instrument of claim 1, wherein the active part is made of tungsten carbide.

3. The instrument of claim 1, wherein the intermediate part is welded to the handle and brazed to the active part.

4. The instrument of claim 1, wherein the intermediate part has a length between 0.05 and 50 mm.

5. The instrument of claim 1, wherein the intermediate part has a length of 1.5 mm.

6. The instrument of claim 1, wherein the rotary cutting instrument is a bur type.

7. The instrument of claim 6, wherein the active part is made of tungsten carbide.

8. The instrument of claim 6, wherein the intermediate part is welded to the handle and brazed to the active part.

9. The instrument of claim 6, wherein the intermediate part has a length between 0.05 and 50 mm.

10. The instrument of claim 6, wherein the intermediate part has a length of 1.5 mm.

\* \* \* \* \*